US008019405B2

(12) United States Patent
Weber et al.

(10) Patent No.: US 8,019,405 B2
(45) Date of Patent: Sep. 13, 2011

(54) DEVICE FOR THE PICTURE-PROVIDING DIAGNOSIS OF TISSUE USING ONE OF AT LEAST TWO DIAGNOSIS MODES

(75) Inventors: Bernd Claus Weber, Karlsruhe (DE); Thomas Goll, Knittlingen (DE); Olaf Schmidt, Vaihingen/Enz (DE); Philipp Eidner, Bretten-Buechig (DE); Stefan Müller, Bretten-Diedelsheim (DE); Hubert van den Bergh, St-Sulpice (CH); Didier Goujon, Fontainemelon (CH); Georges Wagnières, Lutry (CH)

(73) Assignee: Richard Wolf GmbH, Knittlingen (DE)

( * ) Notice: Subject to any disclaimer, the term of this patent is extended or adjusted under 35 U.S.C. 154(b) by 1025 days.

(21) Appl. No.: 10/116,543

(22) Filed: Apr. 4, 2002

(65) Prior Publication Data
US 2002/0147383 A1    Oct. 10, 2002

(30) Foreign Application Priority Data
Apr. 4, 2001    (DE) .................... 101 16 859

(51) Int. Cl.
*A61B 5/05* (2006.01)
(52) U.S. Cl. ........................ 600/478; 600/109
(58) Field of Classification Search ......... 600/309–310, 600/312, 314, 318, 324–325, 342–345, 407, 600/473, 475–479, 436, 317, 101, 109, 112, 600/160, 178, 181; 606/1–4, 10–11, 13–17; 607/1, 88, 92; 250/582–589; 356/300, 302–318, 356/319, 326, 330; 362/574, 583; 385/115–120; 345/603, 589, 619
See application file for complete search history.

(56) References Cited

U.S. PATENT DOCUMENTS

| 4,742,388 | A | * | 5/1988 | Cooper et al. ............... 348/71 |
| 4,957,114 | A | * | 9/1990 | Zeng et al. .................. 600/476 |
| 5,174,297 | A | * | 12/1992 | Daikuzono ................. 600/476 |
| 5,299,306 | A | * | 3/1994 | Asprey ........................ 375/257 |
| 5,452,723 | A | | 9/1995 | Wu et al. .................... 128/664 |
| 5,590,660 | A | | 1/1997 | MacAulay et al. ........... 128/664 |
| 5,647,368 | A | * | 7/1997 | Zeng et al. .................. 600/476 |
| 5,772,580 | A | | 6/1998 | Utsui et al. .................. 600/160 |
| 5,790,096 | A | * | 8/1998 | Hill, Jr. ....................... 345/600 |
| 5,827,190 | A | * | 10/1998 | Palcic et al. ................. 600/476 |
| 6,002,137 | A | * | 12/1999 | Hayashi ..................... 250/458.1 |
| 6,290,645 | B1 | * | 9/2001 | Goldfarb et al. ............ 600/249 |
| 6,422,994 | B1 | * | 7/2002 | Kaneko et al. .............. 600/160 |
| 6,462,770 | B1 | * | 10/2002 | Cline et al. ................... 348/65 |
| 6,498,948 | B1 | * | 12/2002 | Ozawa et al. ................ 600/476 |

(Continued)

FOREIGN PATENT DOCUMENTS
JP    2000-325296    11/2000
(Continued)

*Primary Examiner* — Parikha S Mehta
(74) *Attorney, Agent, or Firm* — Cozen O'Connor (57) ABSTRACT

A device for picture-providing diagnosis of tissue is selectively operated in a picture-providing white light diagnosis mode and a picture providing auto-fluorescence mode. A color camera having red, green, and blue sensors provides a monitor which picture signals. A light source emits fluorescence excitation light and additionally emits so much red light that the red light remitted by the tissue dominates the red fluorescence light in the picture providing auto-fluorescence mode. The signal from the red sensor of the camera is damped so that normal time appears green and pre-malignant and early malignant tissue appears red.

21 Claims, 6 Drawing Sheets

U.S. PATENT DOCUMENTS

| | | | |
|---|---|---|---|
| 6,530,882 B1 * | 3/2003 | Farkas et al. | 600/168 |
| 6,692,431 B2 * | 2/2004 | Kazakevich | 600/178 |
| 6,730,019 B2 * | 5/2004 | Irion | 600/178 |
| 2002/0018036 A1 * | 2/2002 | Karakawa | 345/88 |

FOREIGN PATENT DOCUMENTS

| | | |
|---|---|---|
| WO | WO 95/26673 | 10/1995 |
| WO | WO 99/37204 | 7/1999 |
| WO | WO 00/42910 | 7/2000 |

* cited by examiner

DEVICE FOR THE PICTURE-PROVIDING DIAGNOSIS OF TISSUE USING ONE OF AT LEAST TWO DIAGNOSIS MODES

BACKGROUND OF THE INVENTION

1. Field of the Invention

The invention relates to a device for the picture-providing diagnosis of tissue with the selective application of a picture-providing white light diagnosis mode and a picture-providing auto-fluorescence mode, the device having a light source whose light is led to the tissue by an endoscope, and a picture transmission unit arranged in the endoscope which transmits the picture of the tissue to a colour camera, wherein the colour camera comprises three sensors for the three colour regions red, green and blue which in each case are in connection with a picture processor unit which provides a monitor with the picture signals.

2. Description of the Prior Art

The best chance of healing cancerous lesions is to treat the lesions in the pre-malignant and early-malignant stages of the diseased lesions. The prospects for success with a curative treatment decreases when the lesion reaches the invasive carcinoma stage. Therefore the diagnosis of pre-malignant or early-malignant tissue is of significant importance.

The process of carcinogenesis from the early stage cell types up to the invasive carcinoma stage extends a time-period of several years. This pre-malignant and early-malignant phase therefore offers a large window for diagnosis in which there is given a successful treatment of the patient and tumour-prevention. Unfortunately this time frame until now for therapeutic purposes could only be insufficiently exploited which is reflected is the small five-year survival rate with patients with a bronchial carcinoma which has remained unchanged for decades. This survival rate as always lies only between 10% and 15%.

The reason why these exploitation possibilities in the given long time frame have not been sufficient up to now lies in the fact that the sensitivity of the conventional diagnosis forms—including white light endoscopy—is very small for pre-malignant and early-malignant lesions. Accordingly, many lesions remain undetected using the conventional diagnosis forms.

During the examination of a patient in the bronchial region it is desirable for the physician carrying out the examination to carry out a usual white light diagnosis to obtain an overview of the bronchial region and set up a reference diagnosis. During the examination, the physician searches for inflamed and malignant tissue such as, for example, exophytic tumours, and also for early-malignant tissue inasmuch as this is visible under white light.

With the conventional white light diagnosis, it is difficult to differentiate premalignant and early-malignant tissue from benign tissue which is why it may remain undetected. The white light diagnosis for this has an insufficient sensitivity. Accordingly the necessity of a life-saving or at least significantly life-lengthening therapy may not be recognized. The picture-providing autofluorescence diagnosis represents a decisive advantage over white light diagnosis. Autofluorescence diagnosis considerably improves the visibility or the possibility of differentiating pre-malignant and early-malignant tissue with respect to healthy, inflamed or merely metaplastically changed tissue.

Using picture-providing autofluorescence diagnosis for the diagnosis of pre-malignant or early-malignant lesions, one may ascertain that the healthy tissue differs from diseased tissue in (1) fluorescence intensity integrally over the whole emission range, i.e. in the brightness, and (2) fluorescence colour (the integral colour impression created with the observer, caused by a changing weighting of the spectral components in the fluorescence light emitted by the tissue).

Figure 1:
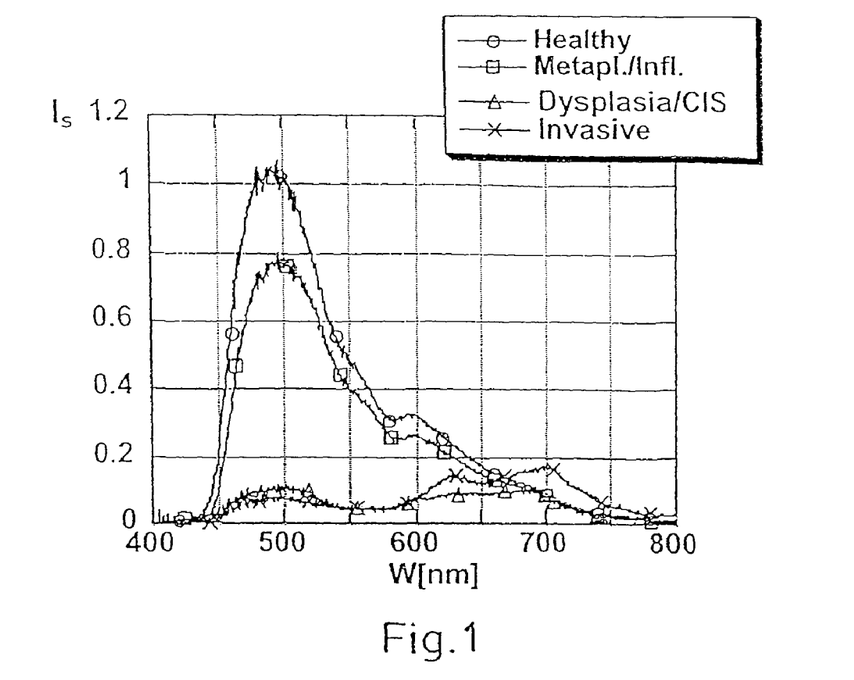
FIG. 1 is a graph showing the spectral fluorescence intensity $I_s$ (random units) over the wavelength W in nanometers for various conditions of tissue.

With regard to the dependency of the fluorescence intensity on the condition of the tissue, FIG. 1 is referred to. Here by way of example for an excitation wavelength of 405 nm the spectral intensity $I_s$ over the wavelength W in nanometers is shown for various tissue conditions (Healthy tissue; metaplastic/inflamed, i.e., non-malignant and therefore tissue types which are not to be graded as malignant; dyplasia/CIS carcinoma in situ; and invasive). From FIG. 1 it is evident that with an increasing degree of tissue atypia or with an increasing degree of malignancy of the integral of intensity reduces.

Figure 2:
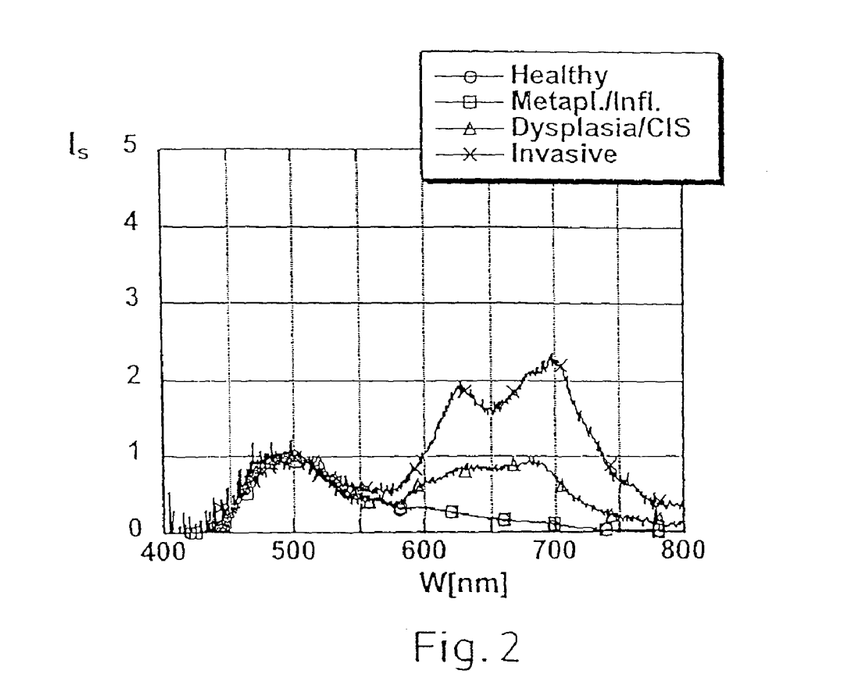
FIG. 2 is a graph showing the course of the curves of the spectral fluorescence intensities $I_s$ of FIG. 1, standardized to the first fluorescence maximum.

The dependency of the fluorescence colour on the tissue condition, i.e. of the integral colour impression created with the observer, is evident from representation according to FIG. 2. Curves of the spectral fluorescence intensities $I_s$ standardized to the first fluorescence maximum are shown for the same sample as in FIG. 1 (the first fluorescence maximum occurs in the green spectral region at approximately 500 nm). The difference to the representation according to FIG. 1 lies merely in the standardization to the highlighting of the colour shifting. The curves for the different condition are however as such identical to those of FIG. 1.

As evidenced by the curves in FIG. 2, tissue having an increasing degree of tissue atypia or with an increasing degree of malignancy has an increased portion of red fluorescence (wavelengths between about 600 nm and 700 nm) relative to green fluorescence (wavelengths smaller than about 570 nm). Therefore, the tissue with an increasing degree of tissue atypia or with an increasing degree of malignancy appears reddish to an increasing amount to the observer.

An evaluation of only the brightness, i.e., the fluorescence intensity, for differentiation of tissue and thus for the diagnosis of pre-malignant and early-malignant lesions (and not evaluating the fluorescence colour) is burdened with problems because a drop of the total fluorescence intensity is not exclusively caused by tissue atypia. The drop in intensity may also be caused on account of tissue morphology. For example microscopically heavily structured but healthy tissue as well as macroscopic surface unevenness, such as possible folds in the tissue with healthy tissue, with regard to the fluorescence excitation light and also with regard to emission of fluorescence light act as "light traps" and by way of this reduce the fluorescence light detectable by the eye or the camera. Thus this type of tissue exhibits a lower intensity similar to diseased tissue.

The evaluation of tissue for pre-malignant and early-malignant lesions alone on the basis of fluorescence intensity alone may therefore lead increasingly to results which are wrongly positive and thus lead to a reduced specifity. Under this aspect with the picture-providing autofluorescence for locating pre-malignant or early-malignant lesions the colour of the tissue dependent on the tissue condition or degree of malignancy and the colour impression thus given to the observer play a decisive role. A picture-providing fluorescence diagnosis system should therefore be designed such that the colour dependent on the tissue atypia, i.e. the change in the weighting of the spectral fluorescence part share, is indeed also made visible to the observer.

FIG. 1 shows that the integral fluorescence intensity of early-malignant and malignant tissue is close to integral fluorescence intensity of healthy tissue. In combination with the finite or limited dynamics of conventional colour cameras and also of the human eye the colour shifting with respect to healthy tissue under certain circumstances may hardly be perceived or not be perceived at all. The suspected location may appear to be only darker. Similarly, colour as well as colour shiftings are to be recognized only in a limited manner. The increased brightness of the healthy tissue surrounding the suspect location acts in an irradiated manner such that colour changes, particularly with smaller suspect locations, may also not be perceived.

The difference between the fluorescence intensity of pre-malignant and early-malignant tissue (see FIG. 1) which is heavily reduced relative to the fluorescence intensity of healthy tissue may be hidden by the fact that the signals produced by the camera in these tissue regions may already be superimposed by a comparatively great noise.

From this there results problems which may be comparable with those which have already been described above.

Early-malignant and malignant lesions on account of their greatly reduced fluorescence intensity and therefore their colour shifting which is hardly perceivable may hardly be differentiated from that healthy tissue which acts in a light-swallowing' manner due to changed surface structures and which therefore may supply the observer with less fluorescence intensity than normal structured healthy tissue.

The difficulties in assessing such tissue renders obligatory the taking of a sample, in order to detect where possible all potential early-malignant or malignant sources. This reduces the false-positive rate, i.e., the specifity. However, the sample taking incurs additional time and costs. Moreover, additional biopsies necessitated by the samples likewise create additional costs. Furthermore each taking of a sample may lead to bleeding which inhibits further examination.

For including an evaluation of colour shifting into the tissue differentiation under the given circumstances it is a disadvantage that with an increasing degree of malignancy or with an increasing atypia of the tissue not only does the fluorescence intensity in the green spectral region decline but also the fluorescence intensity in the red spectral region—even if less marked (see FIG. 1). From a comprehensive point of view it would however be advantageous when the detected red light with respect to the tissue condition remains unchanged, i.e. remains constant. Furthermore, the red part share led to the observer should ideally be so high that it is clearly dominated by green fluorescence of the healthy tissue so that the healthy tissue appears green to the user, but that this red part share of the fluorescence signal significantly exceeds the signals deriving from the green fluorescence of the diseased tissue, which are smaller that those which come from healthy tissue by a factor of 10 (see FIG. 1), so that the diseased tissue appears red to the observer.

A red part share of the fluorescence signal that is independent of the condition of the tissue would lead to an improvement of the colour contrast between healthy and diseased tissue and thus to an increase of the sensitivity, caused by a significantly improved colour shifting towards the red with diseased tissue with respect to the healthy tissue, and the weakly fluorescing diseased tissue can appear brighter, caused by the then higher red part share. Furthermore a better differentiation of the diseased tissue from that healthy tissue which on account of a microscopically or macroscopically greater structured surface nature swallows light and thus appears darker than "smooth" healthy tissue would be possible. The latter tissue appears dark and the early-malignant and malignant tissue in contrast appears red.

The red fluorescence according to FIG. 1 recedes with an increasing tissue change just as the green fluorescence recedes—even if less pronounced, and the red fluorescence does not have a non-negligible dependency on the degree of tissue atypia. Accordingly, the provision of a red part share independent of the tissue condition may only be effected via an irradiation of the tissue with additional red light (besides the fluorescence excitation light). The red light remitted by way of this from the tissue is in contrast to the red fluorescence largely independent on the degree of tissue atypia. At the same time however one must ensure that the signal differences caused by the red fluorescence with different tissue conditions are eliminated or at least are almost without significance with respect to the signal in the red channel produced by the red emission.

U.S. Pat. No. 5,590,660 discloses a diagnosis system with which red light provided by a light source and then remitted at the tissue is used for tissue assessment, and specifically additionally to the fluorescence light emitted by the tissue. The system and the light source are designed so that an improved colour differentiation and thus an improved sensitivity of pre-malignant and early-malignant tissue is achieved relative to a device without adding red light with a light source. The colour impression and thus the tissue condition are only evaluated on the basis of the autofluorescence of the tissue. However, a detection unit having two cameras must be applied, in front of whose sensors there are mounted optical band-width filters which represent specially manufactured products in that they do not correspond to the filter specifications of conventional 3-chip cameras suitable for white light endoscopy. The idea on which U.S. Pat. No. 5,590,660 is based is specifically that the whole detected wavelength region is divided up into two separate spectral regions: a first wavelength region in which essentially the whole autofluorescence light lies (wavelengths between 500 nm and 650 nm; according to the sensitivity of the sensors used here the autofluorescence signal detected above 650 nm is disappearingly small) and a second wavelength region (which does not intersect with the first wavelength region), in which spectrally there lies the additional illumination light from the light source (red light, wavelengths greater than 700 nm). The auto fluorescence signal is led to a first camera whose signals are led to a first color input of a monitor and the remitted red light is led to a second camera whose signals are led to a second colour input of the monitor (e.g. red).

In U.S. Pat. No. 5,590,660, the signal supplied to the second colour channel of the monitor is independent of the degree of tissue atypia (with the advantages with respect to the colour differentiation described in detail above) since the detection region of the second camera which delivers signals to this second monitor input lies outside the wavelength region of the emitted tissue autofluorescence signals whose intensity in turn is dependent on the condition of the tissue. A signal derived from the auto fluorescence and dependent on the tissue condition may not be superimposed on the second signal which is constant with respect to the tissue condition. Accordingly, the second channel may with a suitable metering of the additional illumination light be used as a colour reference with respect to the tissue condition dependent fluctuations of the signals fed into the first channel.

A disadvantage of U.S. Pat. No. 5,590,660 is that the cameras to be used or their sensors may not be part of a conventional 3-chip camera since the first detection region comprises the wavelength region of the whole autofluorescence light which consists of green light but also of red light, whilst the second detection region does not intersect with this first region and accordingly may only lie in the long-wave red spectral region. A conventional 3-chip camera however separates red from green already in a considerably more short-wave region. Thus if a white light diagnosis is carried out with a 3-chip camera then a further conventional colour camera is necessary. The device of U.S. Pat. No. 5,590,660 is necessarily complicated, awkward to use, and expensive. The fact that the wavelength region led to the first camera is so wide or reaches so far into the red spectral region is disadvantageous in that tissue differentiation between the fluorescence curves for the different tissue conditions towards the longwave region, in particular where the yellow and red spectral region approach one another, becomes more and more washed.

Furthermore, U.S. Pat. No. 5,772,580 discloses a diagnosis system which does away completely with the detection of red light with the assessment of tissue, i.e. does away with the red fluorescence as well as additional red light provided by the light source and remitted at the tissue. The transmission region of the sensor applied here lies between 480 nm and 600 nm. Although an increased sensitivity for pre-malignant or early-malignant lesions is achieved, there arise the above mentioned disadvantages entailed when one makes do without the red reference such as the reduced specificity by way of an increased false-positive rate. Although a white light diagnosis is possible, a second camera is necessary. Furthermore making do without the detection of red light (fluorescence as well as red light remitted at the tissue) means a loss of brightness. Thus the system therefore also uses large, heavy and awkward image intensifiers in order to achieve a sufficiently bright picture.

Other diagnosis devices detect blue light instead of additional red light emitted by the light source and remitted at the tissue with the aim of an improved light contrasting of the tissue in the diagnosis mode of the autofluorescence. According to this device, a smaller part share of the blue light made available by the light source for fluorescence excitation which is not absorbed by the tissue but is remitted at the tissue is detected by the camera and not, as with the other known systems, completely blocked (for example by optical filters). At the same time the blue part share reaching the camera by way of optical filter technology is specified such that healthy tissue appears green to the observer and diseased tissue appears bluish. The assessment of the degree of disease of the tissue is effected thus essentially by the assessment of the different green-blue part shares. This method is disadvantageous because, in contrast to red light, blue light has a lower tissue penetration depth. The directly reflected part share of the blue light remitted by the tissue is larger than with red light. Accordingly, the homogeneously scattered back part share of the blue light is less than with red light. Since the tissue fluorescence light however is emitted relatively homogeneously almost independently of the incidence angle of the excitation light (isotrope), the colour impression at the observer arising from the sum of the fluorescence and the blue light remitted at the tissue is heavily dependent on the angle of incidence of the excitation and illumination light, and specifically much greater than with the detection of fluorescence light and of red light remitted by the tissue. The tissue assessment is thus dependent on the incidence angle of the illumination and excitation light which of course is not at all desirable.

BRIEF SUMMARY OF THE INVENTION

It is therefore an object of the invention to provide a diagnosis device for the picture-providing diagnosis of tissue—in particular for the examination of the bronchial region of a patient—with the selective application of the picture-providing white light diagnosis and the picture-providing autofluorescence diagnosis. The mode of the picture-providing autofluorescence diagnosis has an increased sensitivity, i.e., an improved colour contrasting and thus an improved differentiation between healthy and pre-malignant or early-malignant tissue. In the mode of the autofluorescence diagnosis only, the assessment of the autofluorescence light itself is used which permits an increased specifity, i.e., an improved differentiation possibility of pre-malignant and early-malignant tissue above all also with respect to healthy tissue having an uneven structure and therefore light-swallowing surface which leads relatively little fluorescence light to the receiver. At the same time additionally the colour impression of the tissue arising at the observer in the autofluorescence mode is to be largely independent of the observation angle, i.e. of the angle of the endoscope with respect to the surface of the tissue. Furthermore it is to be possible to be able to fall back on existing diagnosis devices without having to make significant modifications. This means above all things that for both working modes as a detection unit there may be applied a 3-chip camera which is conventional with regard to the optical specifications of the camera head. The retention of the optical specifications means that in the working mode of the white light diagnosis the picture does not undergo any compromise and retains its usual good colour quality. Furthermore the system is to be constructed such that a simple change between the picture-providing white light diagnosis and the picture-providing autofluorescence diagnosis may be realized.

For achieving this solution the inventive device includes a light source in the operating mode of the picture-providing autofluorescence diagnosis that is separate from the fluorescence excitation light and additionally further emits red light. The picture processor unit of the camera contains means with which the electrical signals produced by the "red sensor" of the 3-chip camera in the operating mode of the picture-providing autofluorescence diagnosis may be damped. The extent of the damping is coupled to the intensity of the additionally emitted red light, or is dependent on the relation between the fluorescence excitation light and additionally provided red light. The aim is for the red part share of the light detected by the camera to be practically independent of the degree of the tissue atypia and may be used as a reference with respect to the green part share which is very greatly dependent on the degree of the tissue atypia, in order thus amongst other things to realise an improvement of the colour contrast between benign and pre-malignant or early-malignant tissue. With these measures the sensitivity as well as the specifity of the diagnosis device may be increased while simultaneously retaining a more simple construction with regard to the apparatus. The picture-providing representation in both working modes may be carried out by way of a 3-chip camera which is conventional with regard to the optical properties of the head. The colour reproduction of the tissue in the working mode of the picture-providing autofluorescence diagnosis is largely independent of the angle between the tissue normals and the endoscope.

As has already been cited, the colour impression of the tissue which is based on the degree of the tissue atypia or on the degree of malignancy and conveyed to the observer, in the mode of the picture-providing autofluorescence, is based on a heavily increasing decline of the green fluorescence and a less strongly pronounced but unfavourably non-negligible decline of the red fluorescence with an increasing atypia of the tissue. Healthy tissue appears green and pre-malignant or early-malignant tissue with a increasing atypia appears increasingly reddish or red-brown. The colour difference and thus the differentiation capability between benign and pre-malignant or early-malignant tissue would however be more pronounced and clearer if the red part share is approximately the same in each case. Accordingly, the sensitivity of the system with regard to pre-malignant or early-malignant tissue or with an increasing degree of malignancy increases when the red part share does not reduce with an increasing tissue atypia or with an increasing malignancy degree, but for example would remain constant or at least almost constant. In this case, the red part share may comprise a reference function with respect to the tissue condition dependent green part share.

The fluorescence excitation light source not only makes available fluorescence excitation lighbut additionally includes red light that this lead to the tissue to be examined. The autofluorescence excitation in the bronchial region is typically violet/blue light.

Since the design according to the invention includes conventional 3-chip cameras (conventional with respect to optical properties), the camera may be used for usual white light endoscopy, the light incident in the camera head being split up into "blue light", "green light" by dichroitic filters and "red light" and then led to different sensors. Since practically no blue light is induced with the autofluorescence excitation used here, the blue channel in this working mode is subsequently not further observed. The "red sensor" of a 3-chip camera with a conventional camera head, or the optical filter mounted in front of the "red sensor", is specified such that it not only detects the red illumination light which is additionally provided by the light source and remitted by the tissue and independent on of the degree of tissue atypia, but simultaneously also detects the red fluorescence light dependent on the malignancy degree. The filter determining the spectral detection range of the sensor begins usually already at wavelengths which are smaller than 600 nm. At these wavelengths the autofluorescence of the tissue is however still not at all negligably small and the signal processed in the red channel of the camera and made available to the monitor, i.e., the sum of the fluorescence signal and the remission signal, is therefore subjected to fluctuations caused by the condition of the tissue, which cause fluctuations of the fluorescence light. If in spite of the use of a conventional 3-chip camera a red signal practically independent of the type of atypia of the tissue is to be realized then the part share made available in the red spectral region by the light source must dimensioned sufficiently high so that the red light remitted by the tissue, whose intensity is independent of the malignancy of the tissue, dominates the red fluorescence light dependent of the malignancy degree of the tissue by a multiple factor. In other words, the degree of transmission of the fluorescence excitation filter in the light source in the red spectral region is to be selected so high that the red fluorescence light relative to the red light which originates from the light source and which is remitted at the tissue does not play any role or only a negligible role. As the part share of the remission light with respect to the fluorescence light of the whole red light detected by the camera increases, the degree of independence of the red channel signal led to the monitor becomes greater on the degree of tissue atypia. The greater the independence of the detected red light on the degree of tissue atypia the better is the possibility of the differentiation of pre-malignant or early-malignant tissue from healthy tissue (greater red shifting at early-malignant or malignant tissue with respect to the benign tissue).

Simultaneously however in a second step in the diagnosis mode of the picture-providing autofluorescence, the red amplification of the camera must be reduced or the red signal damped—according to the intensity of the additional red light or according to the ratio of the fluorescence excitation light (in the blue/violet) to the additional red light. The high intensity of the additional red light, which is selected sufficiently high so that the red fluorescence with respect to the red remission at the tissue becomes negligible or almost negligible, and the accordingly strong red remission at the tissue would otherwise—without reduction of the red amplification or without damping of the red signal in the camera—dominate the green fluorescence of diseased tissue and the healthy tissue such that the tissue would in each case appear indeed red or at least reddish. This would worsen the differentiation on account of the transmitted colour impression.

The reduction of the camera red amplification or the damping of the red signal in the mode of the Picture-providing autofluorescence diagnosis is effected such that the superposition of tissue fluorescence and of red light additionally provided by the light source and remitted by the tissue leads to the healthy tissue appearing green (which is synonymous with a dominance of green fluorescence with respect to the red emission independent of the tissue condition—the red fluorescence now no longer plays a minimal role) and premalignant or early-malignant tissue appears red (which amounts to a dominance of the red emission independent of the tissue condition with respect to the greatly reduced green fluorescence of diseased tissue in comparison to health tissue). Quantitatively therefore the red channel signal determined essentially by red light remitted at the tissue after the damping in the camera lies between the green channel signal which is produced by green fluorescence light from health tissue and the green channel signal which is produced by the green fluorescence light from diseased tissue.

This inventive procedure significantly increases the sensitivity for detection of pre-malignant or early-malignant tissue compared to when only fluorescence light and no red light additionally emitted from the illuminating and fluorescence exciting light source and remitted at the tissue is detected.

The red part share detected by the camera is now no longer or at least minimally dependent on the malignancy degree of the tissue and therefore no longer or is only minimally reduced by an increasing degree of malignancy, diseased tissue. This produces a more clearer red shifting and, with a suitable setting of the camera damping, irradiates more strongly (since the camera damping ideally is set such that the constant red part share remitted by the tissue and constant with regard to tissue atypia produces a clearly stronger signal than the reduced red fluorescence with diseased tissue). Accordingly, the diseased tissue appears in a stronger red and the colour of the diseased tissue may be perceived brighter and thus better than when exclusively fluorescence light is observed.

The light source may be found in many different embodiments. According to a first embodiment form, the light source consists of a white light source, i.e., a broad-band lamp emitting over the whole visible spectral region, which delivers its light at least partly via an optical filter which permits a light transmission in the blue/violet spectral region and in a spectral region in the red. Alternatively, the light source may consist of a blue-light filtered white light source and an additional red light source. This additional red light source may for example be a red light laser, e.g., a semiconductor laser, or also a red LED or an array of red LED's. Furthermore the light source may consist of a blue/violet light laser and of a red light laser. In this case, a green light laser may be provided which together with the blue and red laser produces a white light for performing a white light diagnosis. In order to realise a colour reproduction in the white light mode which is improved with respect to the version with lasers, an array of relatively broad-band light diodes emitting in different spectral regions may also be used which as a sum ideally cover the whole visible spectral region.

With the device according to the invention there is provided an optical conventional 3-chip camera (the camera being conventional with respect to the optical specifications of the camera head). The camera may comprise a CCD camera or a CMOS camera. Preferably the means for damping the signal originating from the red picture part share in the mode of the autofluorescence diagnosis are controlled by software so that the connection and disconnection of the damping on changing between white light diagnosis and autofluorescence diagnosis function is controlled by a processor. Specifically the means for damping the signal originating from the red picture part share is a voltage controlled amplifier (VCA). Finally between the picture processor unit and the monitor there may be arranged a picture memory which is applied with a picture brightness which is too small.

DETAILED DESCRIPTION OF THE INVENTION

Figure 3:
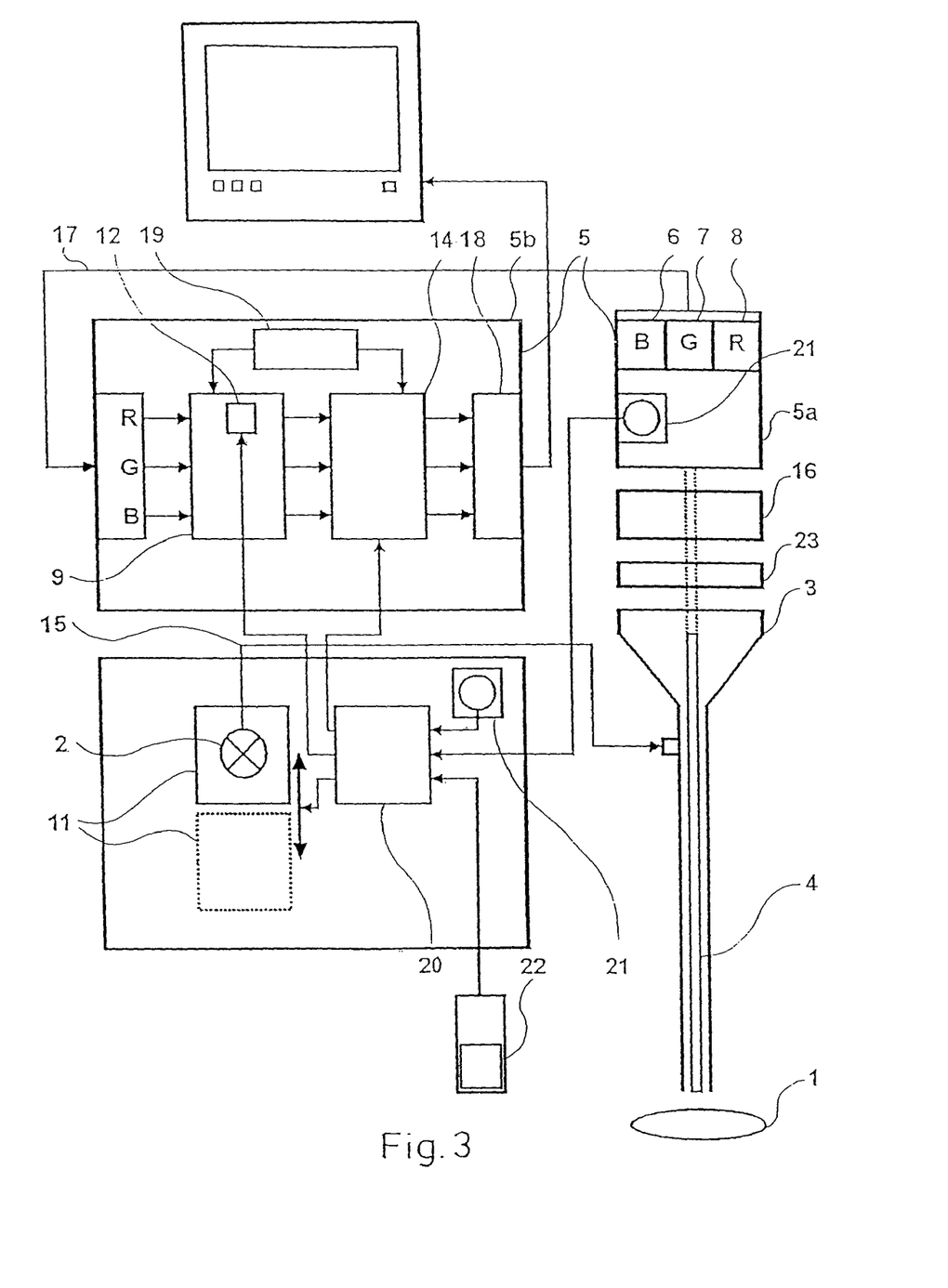
FIG. 3 is a schematic diagram showing a diagnosis device according to an embodiment of the present invention.

FIG. 3 shows a diagnosis device for the combined picture-providing white light diagnosis and picture-providing autofluorescence diagnosis of tissue 1. The device for examining the tissue 1 comprises a light source 2, wherein an incoherent, broad-band light source emitting in the visible spectral region is particularly suitable. The light source 2 emitting preferably white light may be a short arc lamp such as, for example, a xenon lamp a gas discharge lamp with mercury part shares or a mercury high pressure or even mercury highest pressure lamp. The latter have a broad irradiation base continuum in the visible and the line typical for mercury in the blue and violet. These partly ideally lie in the absorption spectrum for fluorescence excitation of the body-intrinsic fluorochrome relevant to the autofluorescence diagnosis. Alternatively a halogen lamp may be used.

All mentioned lamps have the advantage that on the one hand they have an irradiation part share in the violet/blue and (even if small with some lamps) part shares in the red, and on the other hand are in the position of emitting white light. These lamps offer thus ideal conditions for a system which is to permit conventional white light diagnosis a well as autofluorescence diagnosis.

In the examination mode of white light diagnosis the light of the light source 2 via a fibre-optic 15 (i.e., single fibre, fibre bundle or fluid light cable) reaches the endoscope 3. For coupling in the light into the fibre optic 15, the light source 2 may be designed as a reflector lamp or a condenser arrangement. The endoscope 3 leads the light in the known manner to the tissue 1. By way of a picture transmission unit 4, the picture of the tissue 1 is led to the camera head 5a of a camera 5 by a video objective 16. The camera 5 consists of a camera head 5a and of a camera controller 5b. The picture transmission unit 4 includes conventional lens systems, GRIN lens systems, or picture fibre bundles for leading the picture of the tissue to the camera head 5a. To make the comparatively weak autofluorescence light visible at all with respect to the strong intensity fluorescence excitation light remitted at the tissue in the auto fluorescence diagnosis mode, a fluorescence excitation light block filter 23 is arranged somewhere in the picture channel, for example between the endoscope 3 and the video lens 16. This ensures that the fluorescence excitation light remitted at the tissue does not reach the detection unit of the camera. This block filter may either be rigidly attached or pivotable into and out of the beam path.

The camera 5 (above all with respect to the optical properties) is a conventional 3-chip camera which comprises three sensors 6, 7 and 8 which are allocated to the three spectral colour regions blue (B), green (G) and red (R). The camera 5 may thus without limitation, above all without comprising the colour reproduction, be used for conventional white light endoscopy. It may be designed as a CCD camera or as a CMOS camera. A beam-dividing unit in the camera head 5a in the known manner for 3-chip cameras breaks up the picture of the tissue 1 arriving here into the three spectral regions "blue" (B), "green" (G) and "red" (R) and image this onto the sensors 6, 7 and 8.

Via the signal leads 17 the signals of the three sensors 6, 7, 8 are led to a picture processor unit 9. From here the picture signal is led via a picture memory 14 which need not be activated in the mode of the white light diagnosis, and an interface 18 to the monitor 10, via which the physician may view the picture of the tissue 1. A CPU 19 in the camera controller 5b controls the picture processor unit 9 and the picture memory 14. The picture memory and the picture processor unit outputs the previously stored picture when the sensors are not read out, i.e., when fluorescence signals are too weak in the autofluorescence diagnosis. If the illumination or fluorescence excitation chain functions efficiently enough from the light source to the tissue 1, for example by way of the use of a high-transmitting fibre-optic 15 with the best possible adaptation of the elements in the illumination of fluorescence excitation chain amongst one another, and if a camera 5 with a high sensitivity is applied, then under certain circumstances the picture memory 14 may be omitted.

The device further comprises a control unit 20 for controlling or switching the diagnosis mode. The following describes how to switch over from the mode of the white light diagnosis to the mode of the picture-providing autofluorescence diagnosis.

The physician actuates a hand switch 21 or a foot switch 22. The switch signal is led to a control unit 20. This first ensures that a fluorescence excitation filter 11 is brought into the beam path of the light source 2. In this manner the tissue 1 is irradiated with fluorescence excitation light and red light. The tissue is thus irradiated with fluorescence excitation light as well as additionally with red light. At the same time the red transmission of the filter 11 is selected so high that the red fluorescence of the tissue excited by the violet/blue fluorescence excitation light may be neglected with respect to the red light remitted at the tissue, or at least play a very minor role, for example lie in the scale of 1:10 or greater. A ratio of fluorescence light to remitted light of 1:5 or higher may also be sufficient.

Simultaneously, the control unit 20 activates means 12 in the camera for damping the signal value produced in the red channel. Since in the mode of the autofluorescence diagnosis less light reaches the camera 5 than with white light diagnosis, several video frames may be integrated. Furthermore, the picture memory 14 is activated in order to produce an adequately bright picture on the monitor which however is not so grainy.

The renewed actuation of the switches 21 or 22 cancels the above-mentioned measures so that one may switch back from the mode of the picture-providing autofluorescence diagnosis to the white light diagnosis.

In the picture-providing autofluorescence diagnosis the tissue 1 to be examined—in contrast to the "conventional" autofluorescence diagnosis with which only the autofluorescence light itself is detected and assessed—is additionally irradiated with red light and the light remitted at the tissue is used for the tissue assessment using a conventional 3-chip camera (conventional camera head, no change of the head filter specifications). The filter 11 in the light source transmits blue/violet light as described and red light. Alternatively, a separate light source 2a, for example a red light laser, may be applied for transmitting the red light.

Figure 4:
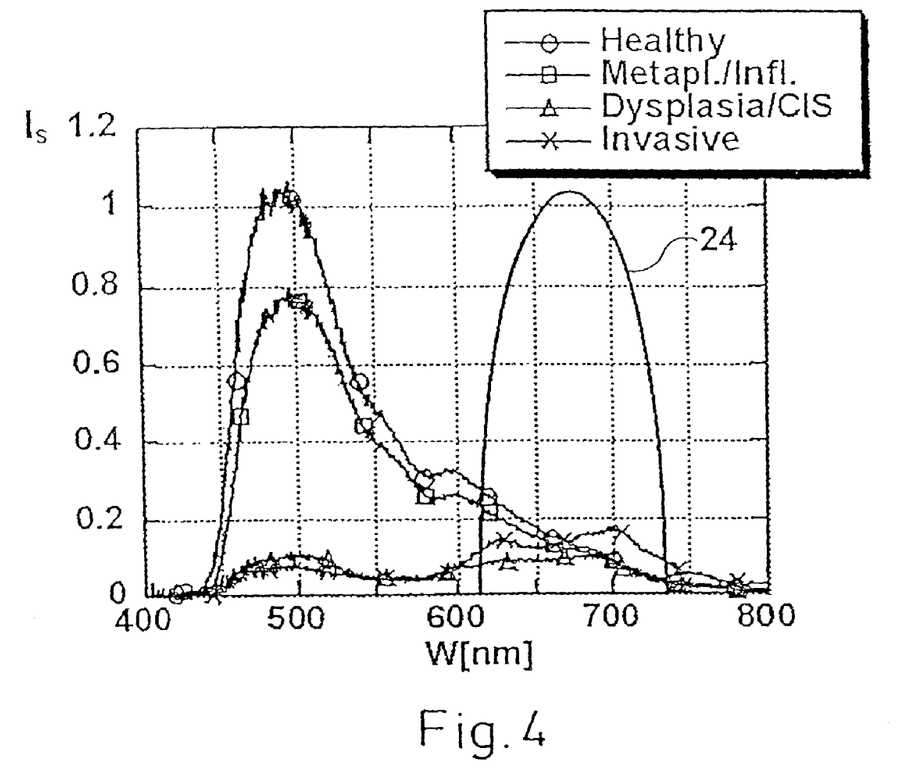
FIG. 4 is a graph showing the spectral fluorescence intensity $I_s$ over the wavelength W in nanometers for various tissue conditions as well as a possible embodiment form of the spectral intensity $I_s$ of the red light superimposed on the fluorescence, emitted by the light source and remitted by the tissue.

FIG. 4 shows the spectral intensity $I_s$ of the tissue fluorescence triggered by the fluorescence excitation light for an excitation wavelength of 405 nm for different tissue conditions and shows the spectral intensity $I_s$ of the red light remitted from the tissue triggered by the red light additionally made available by the light source and led to the tissue. The remitted red light is independent of the tissue condition.

The curves represent the fluorescence spectra as they are detected in the camera head. Additionally drawn in and indicated at 24 is the red light which is additionally provided by the light source and remitted at the tissue, as it is detected at the "red sensor" 8 of the camera. The sketched spectral intensity $I_s$ of the detected additional red light, i.e. the course over the wavelength, only represents a possible example which meets the demands according to the invention of producing a red signal (red reference) practically independent on the degree of tissue atypia. The red light 24 represents the signal at the output of the conventional 3-chip camera or on the monitor in the autofluorescence diagnosis mode. The red light additionally provided by the light source 2 via the filter 11 or alternatively via an additional red light source, and then remitted by the tissue is selected sufficiently strong and intensive so that with the sum of red light arriving at the "red sensor" 8 of the camera consisting of additionally provided red light remitted at the tissue and of tissue red fluorescence produced by blue/violet excitation light, is only minimally or not affected by tissue-dependent fluctuations of red fluorescence no. Thus the larger the light quantity of the additionally provided red light which is remitted at the tissue, the greater is the total red light detected by the camera independent of the degree of tissue atypia. Thus, the red fluorescence and thus also its fluctuations dependent on tissue condition has a minimal or no effect. Therefore a constant red signal is produced independent the degree of tissue atypia.

A quantitative upper limiting of the provided additional red light in practice merely has the effect that the "red sensor" is not to go into saturation, i.e. that the red light arriving at the "red sensor" ideally should lie in dimensions of the green fluorescence arriving at the "green sensor".

Figure 5:
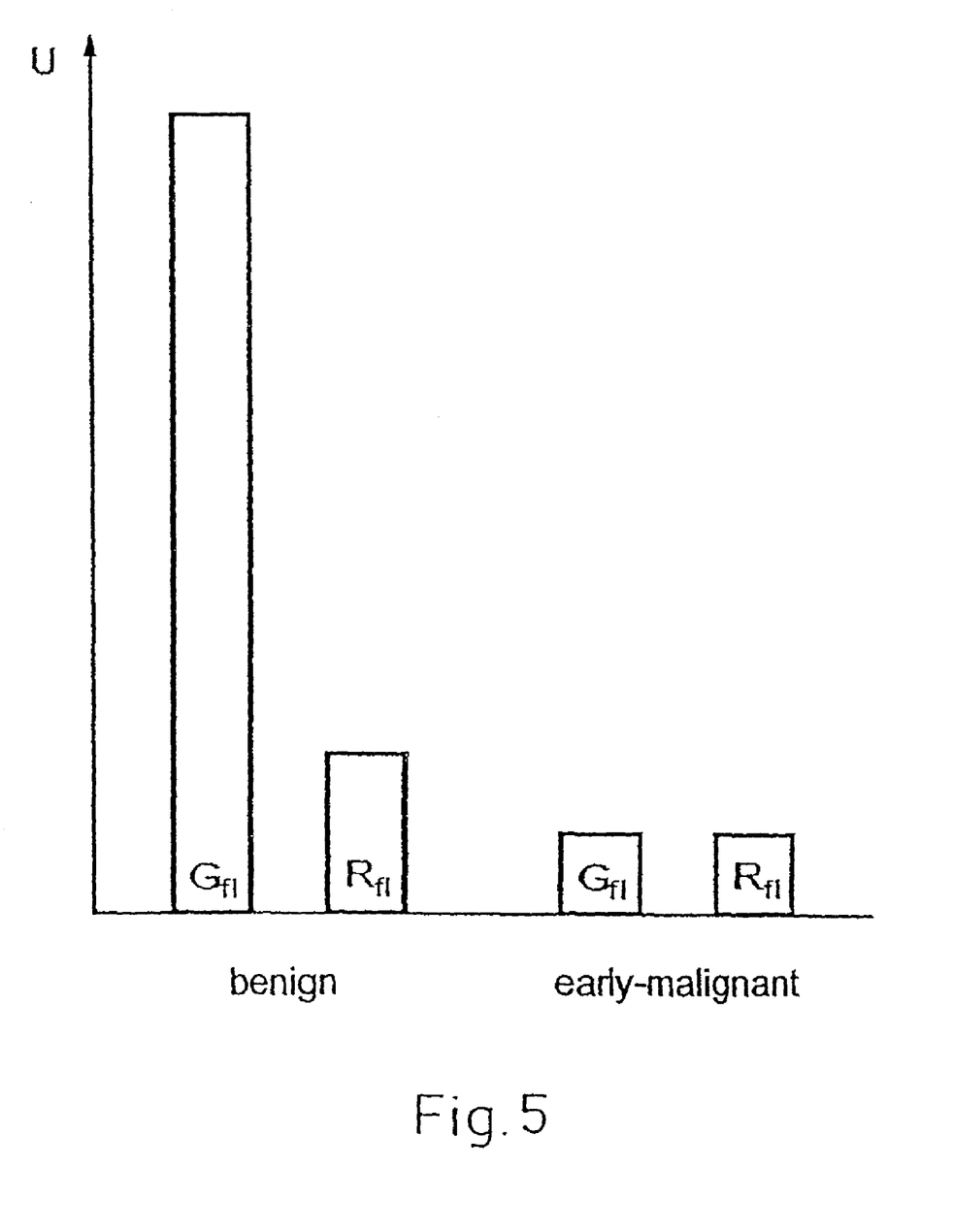
FIG. 5 is a bar graph showing the voltages U for benign and early-malignant tissue produced alone by way of single detection of autofluorescence light from the colour channels (red and green) of the 3-chip camera.
Figure 6:
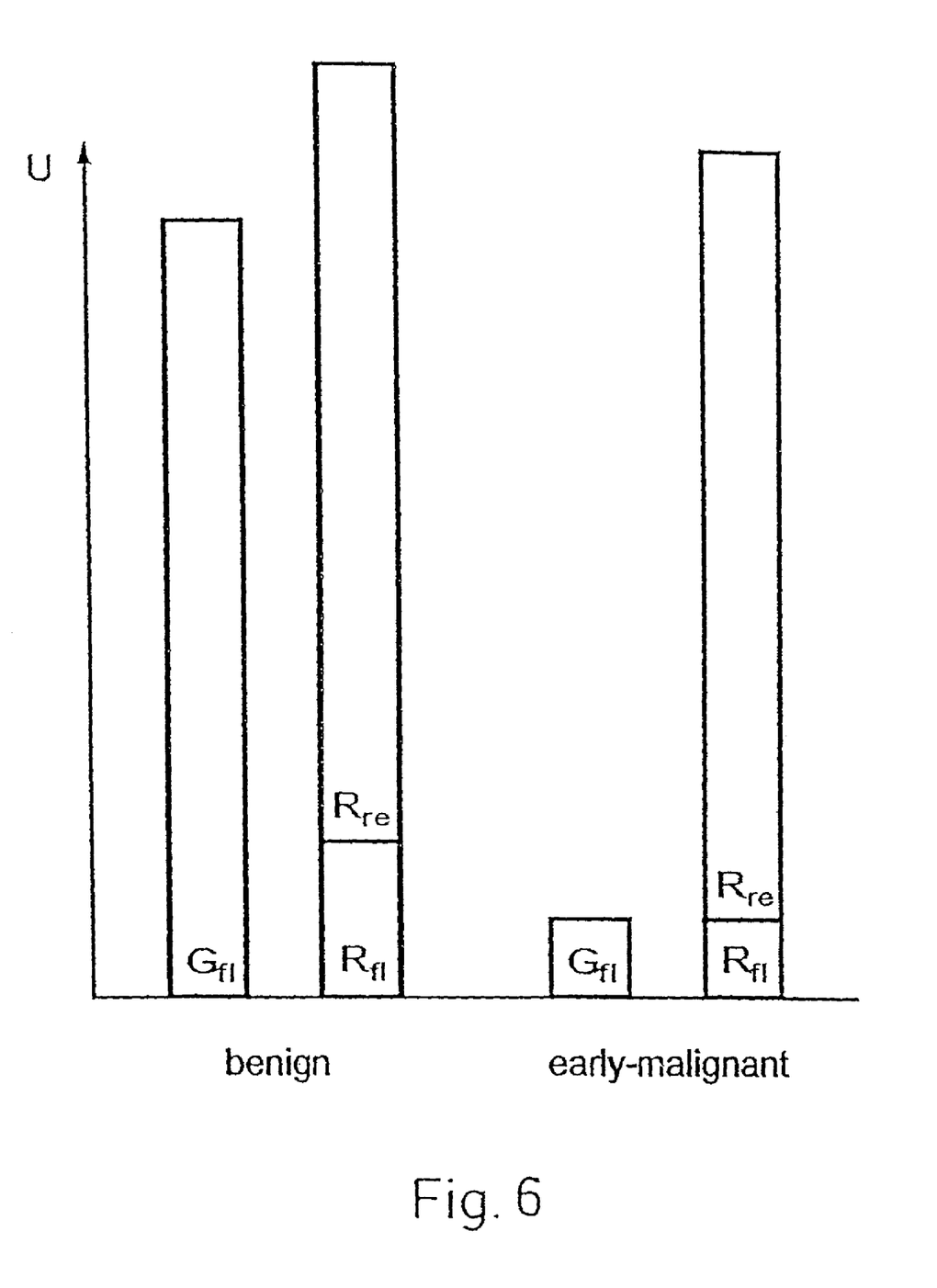
FIG. 6 is a bar graph showing the voltage U for benign and for early-malignant tissue produced by way of detection of autofluorescence light and additionally provided red light from the colour channels (red and green) of the 3-chip camera.
Figure 7:
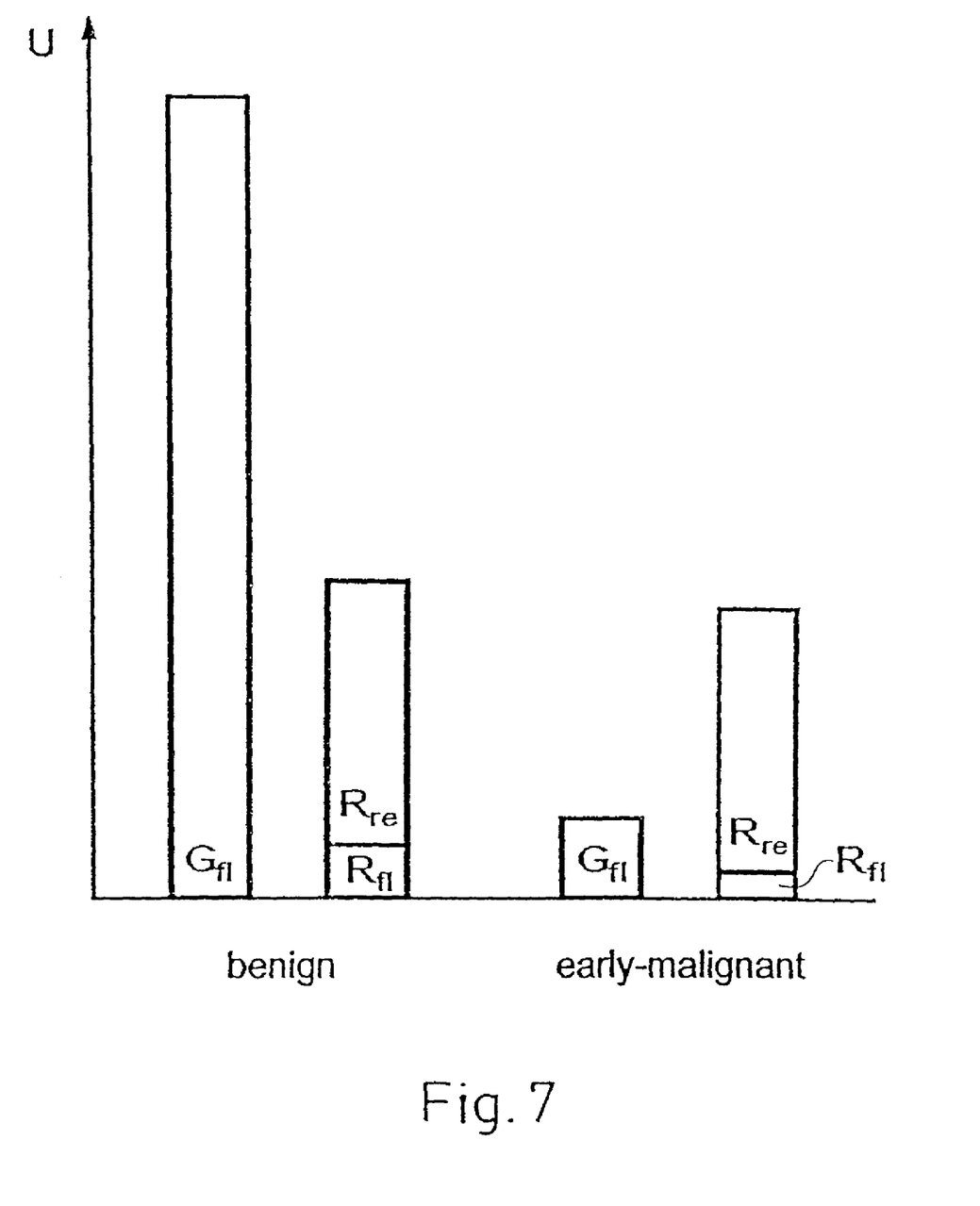
FIG. 7 is a bar graph showing the voltages produced by detection of autofluorescence light and additionally provided red light from the colour channels (red and green) of the 3-chip camera, after damping in the red channel, for benign and early-malignant tissue.

In FIG. 6 there are schematically and qualitatively shown the colour signal ratios resulting therefrom in the camera. FIG. 5 represents in contrast the colour signal ratios in the camera with that manner of proceeding with which the tissue is not irradiated with additional red light. The shown voltage ratios for FIGS. 5 and 6 as well as for the subsequently explained FIG. 7 are based on the curves of FIG. 1 and the surface part shares limited by the courses of these curves. The influence of the spectral sensitivity of the different components being used and under certain circumstances an accordingly demanded weighting of the curves of FIG. 1 are not taken into account here. This influence however may be corrected to an extensive degree by suitable additional amplification or damping in the individual colour channels.

In all three FIGS. 5, 6 and 7) the voltages U of the colour channels green (G) and red (R) (as mentioned blue in the mode of the autofluorescence play no role) are shown against one another for benign and early-malignant tissue. With this the suffix "fl" indicates that the voltage originates from tissue fluorescence light whilst the suffix "re" indicates that the voltage is based on light remitted at the tissue.

FIG. 5 shows the signal voltages U produced in the individual sensors without the additional red light. With early-malignant tissue the red signal is comparable to the green signal. The red shifting desired for a good colour contrasting is thus not present with this tissue condition. A red signal amplification is not favourable for two reasons: (1) the red signal with healthy tissue is increased by the same factor and (2) the red fluorescence with early-malignant and malignant tissue is weak in intensity and therefore the signal-noise ratio is comparatively small. Regarding the first reason, increasing the red signal of a healthy tissue leads to a reduction in the dominance of the signal produced by the green fluorescence light with respect to the signal produced by the red fluorescence light. On the monitor, therefore, the healthy tissue with an increasing red channel amplification appears increasingly reddish, an optimal lifting of the colour contrast is thus not possible in this manner. Regarding the second reason amplification of the red channel therefore leads to a worsening of the total picture quality.

FIG. 6 shows the signal voltages produced in the sensors when the tissue is irradiated with additional red light in the manner that the signal voltage produced by the red light remitted at the tissue clearly dominates that which is produced by the red fluorescence light. Onto the signal voltage bar $R_{fl}$ resulting from the red fluorescence there is placed the signal voltage bar $R_{re}$ resulting from the red light transmission, since the two signal voltages in each case add up.

The additional irradiation of the tissue with red light in the above described manner makes the red light remitted at the tissue equal to or more intensive than the green fluorescence of healthy tissue. If therefore no further measures in the camera were to be made, the tissue imaged on the monitor would always appear red or at least reddish, independent of the condition of the tissue. Thus the additionally sought-after improvement of the colour contrasting of healthy and diseased tissue would not be realized.

For this reason, the electrical total red signal, thus the total voltage produced in the "red sensor" of the 3-chip camera is dampened by the means 12 (see FIG. 3) sufficiently so that on the monitor connected to the camera healthy tissue appears clearly green and diseased tissue clearly red.

The amount of damping of the red part share by the means 12 may be set once and for all before setting the diagnosis system into operation. For example, one may proceed such that the red damping in the camera controller 5*b* is set such that the voltage value obtained from the red channel in a first approximation corresponds to the mean of the two voltage values for healthy and diseased tissue at the green channel.

FIG. 7 shows the signal voltages produced in the sensors after the red channel voltages of FIG. 6 by way of example have experienced the additionally required damping in a manner such that the benign tissue appears clearly green and the diseased tissue clearly red.

Therefore, the electrical signal produced by the light in the sensors (i.e., the "red sensor") is influenced instead of the detected light. However in the sensor itself or at its output a spectral breakdown of the signal is no longer possible. Instead, the output of each sensor (red, green, blue) is in each case only one time-dependent signal value. Therefore in the FIGS. 5, 6 and 7 there are only drawn voltage bars. A comparison of FIGS. 6 and 7 thus shows by way of example and schematically how the electrical red channel signal with respect to the green channel signal may be set according to the device according to the invention, so that healthy tissue appears green (the voltage at the green channel must clearly dominate the voltage at the red channel) and diseased tissue red (the reduced voltage at the green channel caused by disease must now be clearly dominated by the voltage at the red channel). The comparison of FIGS. 5 and 7 shows how with the measures of the device according to the invention with respect to the mere detection and assessment of fluorescence light a much clearer colour differentiation of the shown tissue conditions may be realized, in that with early-malignant tissue a significant increase of the red channel signal may be realized, without in the same measure increasing the red channel signal with healthy tissue.

The setting, by way of example, of the voltage ratios in the camera via the damping member 12 with the result as is shown in FIG. 7, applies only to the theoretically simplest case that in the remaining transmission chain (camera-monitor-human eye) the red signal and the green signal are transmitted in the ratio 1:1. This is not necessarily the case in practice. Accordingly the bar heights represented in FIG. 7 for the different, spectral sensitivities must be corrected. This may likewise be effected via the damping member 12.

The inclusion of red light remitted from the tissue into the tissue assessment with a simultaneous, accordingly adapted damping of the electrical signals in the red channel of the applied conventional 3-chip camera in the form described here has therefore the following function and advantages. The sensitivity for pre-malignant or early malignant lesions with respect to benign tissue is increased in that the red part share led to the detector is not or only minimally dependent on the degree of tissue atypia (in contrast to the conditions with the pure fluorescence detection) and accordingly ensures an improved colour contrast between benign and early-malignant tissue (the early malignant tissue appears significantly more red with respect to benign tissue).

The red channel signal with this "fixing" to an almost unchangeable value with respect to the degree of tissue atypia has a reference function. Only the change in green fluorescence for the tissue assessment is of importance since indeed ideally the red light led to the camera and thus the observer is almost independent on the tissue condition and is almost constant with regard to this. With a suitably set damping the signal provided from the green channel with healthy tissue is significantly greater and this therefore appears in a strong green, with diseased tissue considerably weaker and the latter therefore appears in a strong red.

If one would alone take this aspect into account (that anyway only the change of the green fluorescence is observed) a complete fading-out of the whole red light would be an alternative to the explained manner of proceeding. The additional effort of fixing filter specifications for the excitation light filter in the red or alternatively an additional red light source whilst maintaining the usual filter specifications as well as an adaptation of the camera to the changed conditions caused by the additional red light would therefore be omitted. The colour impression or the colour shifting in turn would however no longer play a role in the assessment of the tissue, only the drop in intensity in the green would be relevant to the tissue differentiation. As however has already been mentioned, also healthy tissue whose surface on account of morphological unevennesses acts as a "light trap" may cause a similar drop in fluorescence as with pre-malignant or early-malignant tissue, with the result that here a differentiation is hardly possible, which then leads to a drop in the specifity. If however remitted red light in the described manner is included in the tissue assessment, the tissue assessment to the first degree takes place by way of the colour impression given to the observer. This is independent of the surface structure of the tissue since the light trap effect with red light and green light is effective to the same extent, thus is independent of the wavelength and independent of the distance of the endoscope to the tissue. As desired thus alone the degree of tissue atypia effects a colour change. Inasmuch as this is concerned the additionally detected, remitted red light has an important reference function in comparison to a complete foregoing of all red light detection.

Finally the additional red light which is made available by the light source and which is remitted by the tissue in contrast to the measure of completely blanking-out the red light but also—as already explained—in contrast to the mere detection of fluorescence light over the whole spectral region (green and red fluorescence light) has an additional gain in brightness. In contrast to the latter case there exists the possibility by increasing the red light part share given out by the light source and remitted at the tissue of accordingly reducing the red amplification of the picture-recording camera almost to any extent and thus of improving the signal-noise ratio in this spectral region. This is of great importance against the background of fluorescence pictures which are in any case weak and the low sensitivity of common commercial medical cameras in the red region which is as a rule very small with respect to the sensitivity in the green (region) (usually caused by way of an optical filter which is attached on the camera head input and which has with a reducing transmission towards to long-waved red region). Therefore without other measures which limit the picture quality such as electronic amplification or increasing the picture integration time an increase in the brightness in the autofluorescence mode and an improvement of the signal-noise ratio may be achieved.

A further advantage of the described arrangement—in particular with respect to the diagnosis system described in U.S. Pat. No. 5,590,660—lies in the fact that the light producing the green channel signal is determined by the comparatively narrow transmission band of the optical filter in front of the "green sensor' of a 3-chip camera which is conventional with regard to the head specifications. The long-wave transmission "edge" of this filter lies usually in a spectral region of about 580 nm. Only in one region below this wavelength are however the intensity differences between the benign and pre-malignant or early-malignant tissue greatly distinguished. The values for the spectral intensity with healthy and diseased tissue approach one another more and more toward the long-wave region (see FIG. 1). The additional inclusion of light above a wavelength of approx. 580 nm into the green channel as this is provided by the diagnosis system of U.S. Pat. No.

5,590,660 (here up to 650 nm) worsens the contrast between healthy and diseased tissue (with an increasing wavelength) and the possibility of tissue differentiation becomes less favourable.

The inventive device permits the use of a conventional 3-chip camera for both operating modes (white light and autofluorescence) and thus coherently allows the realization of a simple change between the two operating modes of the white light diagnosis and the picture-providing autofluorescence diagnosis. A special sensor and filter design (in the head of the camera) and thus a deviation of the optical head configuration optimal for white light diagnosis is not required, i.e. the camera produces with respect to the picture and colour quantity unlimited good pictures also in the white light mode. Since the diagnosis device only requires one camera for both diagnosis modi, there is created the precondition for a small, light, handy and inexpensive system which has a very good sensitivity and a high specifity.

Since the light additional to the excitation light in the autofluorescence mode and used for increasing the colour contrast lies in the red spectral region, the penetration depth is comparatively high. The directed reflected part share is comparatively low and thus the achieved colour impression of the tissue is almost completely dependent on the angle from the endoscope to the tissue normal in contrast to systems which detect blue fluorescence excitation light and include this in the tissue assessment. The effect may be further increased in that the spectral band of the red light additionally emitted by the light source is selected narrow and is applied onto the long-waved "edge" of the transmission band of the "red filter" in front of the sensor 8.

The invention claimed is:

1. A device for the picture-providing diagnosis of a tissue selectively using one of at least two diagnosis modes including a first mode for a picture-providing white light diagnosis and a second mode for a picture-providing auto-fluorescence diagnosis, said device comprising:
    a light source emitting a light;
    a conventional 3-chip colour camera comprising a red sensor, a green sensor, and a blue sensor for red, green and blue colour regions, respectively;
    an endoscope connected to said light source and configured to lead the light emitted from said light source to the tissue, said light emitted by said light source comprising a fluorescence excitation light and an additional red light when said device is in said picture-providing auto-fluorescence diagnosis mode, wherein said additional red light is configured to cause an intensity of red light remitted by the tissue in said picture providing auto-fluorescence diagnosis mode to be greater than an intensity of red fluorescence emitted by the tissue such that a signal produced by said red sensor in the picture-providing auto-fluorescence diagnosis mode is dominated by the remitted red light and the intensity of the red fluorescence emitted by the tissue is a negligible component of the signal produced by the red sensor;
    a picture transmission unit in said endoscope configured to transmit a picture of the tissue from said endoscope to said colour camera to permit the pictorial diagnosis of the tissue; and
    a picture processor connected to said red, green and blue sensors of said colour camera and a monitor, wherein said picture processor generates picture signals for said monitor from said red, green, and blue sensors in both the picture-providing white light diagnosis mode and the picture-providing auto-fluorescence diagnosis mode, and wherein said picture processor includes means for damping electrical signals, said means for damping electrical signals being configured and dimensioned to dampen electrical signals produced by said red sensor in said picture-providing auto-fluorescence diagnosis mode such that an amplitude of the dampened electrical signals produced by said red sensor is between a range of amplitudes of electrical signals produced by said green sensor in the auto-fluorescence diagnosis mode.

2. The device of claim 1, further comprising a central control unit connected to said picture processor and said light source, wherein the central control unit is configured to coordinate a switch between said first and second modes.

3. The device of claim 2, wherein said means for damping the electrical signals comprises a software controlled device.

4. The device of claim 2, wherein said means for damping the electrical signals is connected to said central control unit and said central control unit activates said means for damping the electrical signals in the picture-providing auto-fluorescence diagnosis mode and deactivates said means for damping the electrical signals in the picture-providing white light diagnosis mode.

5. The device of claim 1, wherein said means for damping the electrical signals comprises a software controlled device.

6. The device of claim 5, further comprising a control unit connected to said picture processor and said light source, wherein the control unit is configured to coordinate a switch between said first and second modes, wherein said means for damping the electrical signals is connected to said central control unit and said central control unit activates said means for damping the electrical signals in the picture-providing auto-fluorescence diagnosis mode and deactivates said means for damping the electrical signals in the picture-providing white light diagnosis mode.

7. The device of claim 1, further comprising a central control unit connected to said picture processor and said light source, wherein the control unit is configured to coordinate a switch between said first and second modes, wherein said means for damping the electrical signals is connected to said central control unit and said central control unit activates said means for damping the electrical signals in the picture-providing auto-fluorescence diagnosis mode and deactivates said means for damping the electrical signals in the picture-providing white light diagnosis mode.

8. The device of claim 1, wherein said light source comprises an incoherent, spectral broad-band source which emits light via an optical filter that permits light transmission in a blue-violet spectral region and in a red spectral region.

9. The device of claim 1, wherein said light source comprises an incoherent, spectral broad-band light source and an additional red light source.

10. The device of claim 9, wherein said red light source comprises a laser light source that emits light in the red spectral region.

11. The device of claim 9, wherein said red light source comprises at least one LED that emits light in the red spectral region.

12. The device of claim 1, wherein said light source comprises at least one LED that emits light in the blue/violet spectral region and a red light source.

13. The device of claim 12, wherein said light source further comprises at least one LED that emits light in the green spectral region.

14. The device of claim 1, wherein said light source comprises a laser that emits light in the blue/violet spectral region and a red light source.

15. The device of claim 14, wherein said light source further comprises at least one LED that emits light in the green spectral region.

16. The device of claim 1, wherein said colour camera comprises a three-chip camera configured for implementation in white light endoscopy.

17. The device of claim 16, wherein said colour camera comprises a CCD camera.

18. The device of claim 17, wherein said colour camera comprises a CMOS camera.

19. The device of claim 16, wherein said red fluorescence at the wavelength of the remitted red light is dependent on tissue atypia, the intensity of said remitted light being sufficiently larger than the red fluorescence such that the signal produced by said red sensor is independent of a specific level of tissue atypia.

20. The device of claim 1, wherein said red fluorescence at the wavelength of the remitted red light is dependent on tissue atypia, the intensity of said remitted light being sufficiently larger than the red fluorescence such that the signal produced by said red sensor is independent of a specific level of tissue atypia.

21. The device of claim 1, wherein said means for damping the electrical signals imparts a damping such that benign tissue appears green and pre-malignant or early malignant tissue appears red on said monitor.

* * * * *